United States Patent
Ohno et al.

(10) Patent No.: US 8,415,516 B2
(45) Date of Patent: Apr. 9, 2013

(54) PRODUCTION PROCESS AND PURIFICATION PROCESS FOR 1,2,3,4-TETRACHLOROHEXAFLUOROBUTANE

(75) Inventors: Hiromoto Ohno, Minato-ku (JP); Toshio Ohi, Minato-ku (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 12/992,822

(22) PCT Filed: May 11, 2009

(86) PCT No.: PCT/JP2009/058772
§ 371 (c)(1),
(2), (4) Date: Nov. 15, 2010

(87) PCT Pub. No.: WO2009/139352
PCT Pub. Date: Nov. 19, 2009

(65) Prior Publication Data
US 2011/0071325 A1  Mar. 24, 2011

(30) Foreign Application Priority Data

May 16, 2008  (JP) .................................. 2008-129476

(51) Int. Cl.
*C07C 17/00* (2006.01)
*C07C 17/38* (2006.01)

(52) U.S. Cl.
USPC .......................................... 570/161; 570/178

(58) Field of Classification Search ................... 570/161, 570/178
See application file for complete search history.

(56) References Cited

FOREIGN PATENT DOCUMENTS

| JP | 07-033695 | * | 2/1995 |
| JP | 2001-247495 | * | 9/2001 |
| JP | 2006-342059 A | | 12/2006 |
| WO | 2004/035518 A1 | | 4/2004 |
| WO | 2007/125975 A1 | | 11/2007 |
| WO | 2008/120642 A1 | | 10/2008 |
| WO | 2008/133086 A1 | | 11/2008 |

OTHER PUBLICATIONS

Toshiaki Akabane, "Batch Plant and Engineering," Kabushiki Kaisha Kagaku Kogyosha, Mar. 25, 1979, pp. 133-138.

* cited by examiner

*Primary Examiner* — Jafar Parsa
(74) *Attorney, Agent, or Firm* — Sughrue Mion, PLLC

(57) ABSTRACT

It is an object of the present invention to provide a process for producing 1,2,3,4-tetrachlorohexafluorobutane industrially inexpensively and efficiently by utilizing expensive fluorine gas efficiently and to provide a process which is capable of stably producing 1,2,3,4-tetrachlorohexafluorobutane and in which, by carrying out fluorination reaction at a low temperature, side reactions such as formation of a low-boiling substance due to cleavage of C—C bonds and formation of an excess fluoride are difficult to occur. The process for producing 1,2,3,4-tetrachlorohexafluorobutane of the present invention is characterized in that it includes feeding fluorine gas to 1,2,3,4-tetrachlorobutane using plural reactors in the presence of a solvent and in the absence of a catalyst to allow the 1,2,3,4-tetrachlorobutane and the fluorine gas to react with each other, wherein a part or all of unreacted fluorine gas discharged from one reactor is introduced into a reactor different from said one reactor.

8 Claims, No Drawings

PRODUCTION PROCESS AND PURIFICATION PROCESS FOR 1,2,3,4-TETRACHLOROHEXAFLUOROBUTANE

CROSS REFERENCE TO RELATED APPLICATIONS

This application is a National Stage of International Application No. PCT/JP2009/058772 filed May 11, 2009, claiming priority based on Japanese Patent Application No. 2008-129476 filed May 16, 2008.

TECHNICAL FIELD

The present invention relates to a production process and a purification process for 1,2,3,4-tetrachlorohexafluorobutane. More particularly, the present invention relates to a process for producing 1,2,3,4-tetrachlorohexafluorobutane that is useful as, for example, a raw material for synthesis of hexafluoro-1,3-butadiene that is attracting attentions as an etching gas for semiconductors or the like, and a process for purifying 1,2,3,4-tetrachlorohexafluorobutane.

BACKGROUND ART 1,2,3,4-Tetrachlorohexafluorobutane is an important compound as a raw material or the like for synthesis of hexafluoro-1,3-butadiene that is attracting attentions as an etching gas for use in fine processing of semiconductors. As a process for producing this 1,2,3,4-tetrachlorohexafluorobutane, a process described in the following patent document has been heretofore known.

In Japanese Patent Laid-Open Publication No. 2006-342059 (patent document 1), a process for producing 1,2,3,4-tetrachlorohexafluorobutane by allowing a compound represented by $CClX^1X^2$—$CClX^3$—$CClX^4$—$CClX^5X^6$ (X is a hydrogen atom or a fluorine atom) to react with fluorine in the liquid phase. In the patent document 1, it is described that in this process, perfluoroalkanes, perfluoroethers, perfluoropolyethers, chlorinated hydrocarbon and perfluoroalkylamines are used as solvents. In the patent document 1, it is also described that use of 1,2,3,4-tetrachlorohexafluorobutane as a solvent for fluorination reaction is particularly preferable because there is an advantage that separation between the solvent and the product is unnecessary. In this process, however, the reaction raw material is diluted with the solvent and fluorination reaction is carried out in a low concentration, so that a problem remains with regard to production of a desired product industrially economically and efficiently.

By the way, in the process in which an organic compound and fluorine gas are allowed to directly react with each other in the absence of a catalyst, it is usually an important point how efficiently and unwastefully expensive fluorine gas is used, in order to economically produce the desired product. In the patent document 1, however, utilization rate of the fluorine gas has not been studied at all.

Also from this viewpoint, therefore, the process for producing 1,2,3,4-tetrachlorohexafluorobutane described in the patent document 1 leaves a problem with regard to production of a desired product industrially inexpensively and efficiently.

It is known that isomers such as optical isomers are present in the 1,2,3,4-tetrachlorobutane. When it is used, without distinguishing between the isomers, in the form of a mixture of isomers as a diluent or a solvent, the reaction temperature is frequently set on the basis of an isomer having a high melting point among the isomers. Therefore, in the case where liquidphase reaction is carried out, the reaction temperature must be occasionally set at a high temperature of certain degree in order to perform reaction while keeping a liquid state. If the reaction is carried out in this way, there occurs a problem that, for example, side reaction to form a low-boiling component proceeds because of cleavage of C—C bonds in the fluorination reaction to thereby lower yield of the desired product or the fluorination reaction proceeds excessively.

Accordingly, in addition to how to utilize the fluorine gas effectively as described above, how to prepare the desired product in a high yield is also a problem to be solved.

CITATION LIST

Patent Document

Patent document 1: Japanese Patent Laid-Open Publication No. 2006-342059

SUMMARY OF THE INVENTION

Problem to be Solved by the Invention

It is an object of the present invention to provide a process for producing 1,2,3,4-tetrachlorohexafluorobutane industrially inexpensively and efficiently by utilizing expensive fluorine gas efficiently.

It is another object of the present invention to provide a process capable of stably producing 1,2,3,4-tetrachlorohexafluorobutane by carrying out fluorination reaction at a low temperature and thereby making it difficult for side reactions such as formation of a low-boiling substance due to cleavage of C—C bonds and formation of an excess fluoride, to occur.

It is a further object of the present invention to provide a process for efficiently purifying the produced 1,2,3,4-tetrachlorohexafluorobutane.

Means to Solve the Problem

That is to say, the present invention relates to the following [1] to [10].

[1] A process for producing 1,2,3,4-tetrachlorohexafluorobutane, comprising feeding fluorine gas to 1,2,3,4-tetrachlorobutane using plural reactors in the presence of a solvent and in the absence of a catalyst to allow the 1,2,3,4-tetrachlorobutane and the fluorine gas to react with each other, wherein a part or all of unreacted fluorine gas discharged from one reactor is introduced into a reactor different from said one reactor.

[2] The process for producing 1,2,3,4-tetrachlorohexafluorobutane as stated in [1], wherein the plural reactors are arranged in series, and a part or all of unreacted fluorine gas discharged from a reactor on the upstream side is introduced into a reactor on the downstream side.

[3] The process for producing 1,2,3,4-tetrachlorohexafluorobutane as stated in [2], wherein a part or all of unreacted fluorine gas discharged from a reactor on the downstream side is further introduced into a reactor on the upstream side.

[4] The process for producing 1,2,3,4-tetrachlorohexafluorobutane as stated in [2] or [3], wherein the plural reactors are two reactors arranged in series.

[5] The process for producing 1,2,3,4-tetrachlorohexafluorobutane as stated in [1], wherein the solvent contains hydrogen fluoride.

[6] The process for producing 1,2,3,4-tetrachlorohexafluorobutane as stated in [1], wherein in 100% by mass of the 1,2,3,4-tetrachlorobutane, a dl form that is an optical isomer thereof is contained in an amount of not less than 40% by mass.

[7] The process for producing 1,2,3,4-tetrachlorohexafluorobutane as stated in [1], wherein the reaction solution containing 1,2,3,4-tetrachlorohexafluorobutane obtained by the reaction of the 1,2,3,4-tetrachlorobutane with the fluorine gas is introduced into a distillation column, the reaction solution is separated into a liquid containing 1,2,3,4-tetrachlorohexafluorobutane and a liquid containing the solvent, and the separated liquid containing the solvent is returned to a reactor for carrying out reaction of 1,2,3,4-tetrachlorobutane with fluorine gas and recycled.

[8] A process for purifying 1,2,3,4-tetrachlorohexafluorobutane, comprising: introducing a reaction solution containing 1,2,3,4-tetrachlorohexafluorobutane obtained in the process as stated in [1] into a distillation column, separating the reaction solution into a liquid containing 1,2,3,4-tetrachlorohexafluorobutane and a liquid containing the solvent, and bringing at least apart of the separated liquid containing 1,2,3,4-tetrachlorohexafluorobutane into contact with an alkaline substance and/or water.

[9] The process for purifying 1,2,3,4-tetrachlorohexafluorobutane as stated in [8], wherein the liquid containing 1,2,3,4-tetrachlorohexafluorobutane which has been brought into contact with an alkaline substance and/or water is further brought into contact with a porous purifying agent.

[10] The process for purifying 1,2,3,4-tetrachlorohexafluorobutane as stated in [9], wherein the porous purifying agent is zeolite.

That is to say, the present invention has been made based on the following two findings.

(1) When fluorine gas is fed to 1,2,3,4-tetrachlorobutane using plural reactors in the presence of a solvent and in the absence of a catalyst to allow the 1,2,3,4-tetrachlorobutane and the fluorine gas to react with each other, a part or all of unreacted fluorine gas discharged from one reactor is introduced into a reactor different from said one reactor, whereby fluorine gas can be used unwastefully, and 1,2,3,4-tetrachlorohexafluorobutane can be produced efficiently and economically.

(2) The 1,2,3,4-tetrachlorohexafluorobutane obtained in this way is separated by one or more distillation columns, then brought into contact with an alkali or the like, and if necessary, further brought into contact with a porous purifying agent such as zeolite, whereby 1,2,3,4-tetrachlorohexafluorobutane can be readily purified.

Effects of the Invention

According to the present invention, reaction of 1,2,3,4-tetrachlorobutane with fluorine gas can be carried out in the low-temperature region, formation of a low-boiling component due to cleavage of C—C bonds can be suppressed, and besides, progress of excess fluorination reaction, etc. can be suppressed. According to the present invention, therefore, expensive fluorine gas can be used unwastefully, and 1,2,3,4-tetrachlorohexafluorobutane can be produced efficiently and economically.

DESCRIPTION OF EMBODIMENTS

The production process and the purification process for 1,2,3,4-tetrachlorohexafluorobutane of the present invention are described in detail hereinafter.

[Process for Producing 1,2,3,4-tetrachlorohexafluorobutane]

The present invention is a process for producing 1,2,3,4-tetrachlorohexafluorobutane in which 1,2,3,4-tetrachlorobutane is used as a starting raw material and to this fluorine gas is fed in the presence of a solvent and in the absence of a catalyst to allow the 1,2,3,4-tetrachlorobutane and the fluorine gas to react with each other.

<1,2,3,4-Tetrachlorobutane>

1,2,3,4-Tetrachlorobutane used as a starting raw material in the present invention is, for example, generated as a side product in the production stage of chloroprene rubber that is industrially produced, as shown in the following chemical formulas. The following formula (1) is a formula representing main reaction in the production of chloroprene rubber. The formula (2) is a formula representing an example of side reaction which proceeds simultaneously with the progress of the reaction represented by the formula (1).

[Chem. 1]

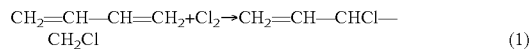

$$CH_2=CH-CH=CH_2+Cl_2 \rightarrow CH_2=CH-CHCl-CH_2Cl \quad (1)$$

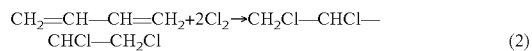

$$CH_2=CH-CH=CH_2+2Cl_2 \rightarrow CH_2Cl-CHCl-CHCl-CH_2Cl \quad (2)$$

In the conventional production of chloroprene rubber, 1,2,3,4-tetrachlorobutane generated by such side reaction as is represented by the above formula (2) is made harmless by incineration treatment or the like and disposed of together with other by-products (chlorination products).

In the present invention, 1,2,3,4-tetrachlorobutane, which, for example, is generated as a by-product and disposed of in the production process of chloroprene rubber as described above, can be used as a starting raw material by separating and recovering it.

Moreover, by means of chlorination reaction of 3,4-dichlorobutene-1 which is an intermediate product in the production process of chloroprene rubber that is a product of the reaction of the aforesaid formula (1), 1,2,3,4-tetrachlorobutane can be also obtained (see the following formula (3)).

[Chem. 2]

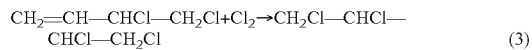

$$CH_2=CH-CHCl-CH_2Cl+Cl_2 \rightarrow CH_2Cl-CHCl-CHCl-CH_2Cl \quad (3)$$

In the case where 1,2,3,4-tetrachlorobutane obtained as above is used as a starting raw material, the purity of the 1,2,3,4-tetrachlorobutane is usually not less than 95% by mol, more preferably not less than 98% by mol. Use of 1,2,3,4-tetrachlorobutane having such a high purity as above as a starting raw material is advantageous from the viewpoint of production because by-products are less produced, separation thereof is facilitated, the purity of the resulting 1,2,3,4-tetrachlorohexafluorobutane becomes high, and excess equipment is not required in the purification process.

1,2,3,4-Tetrachlorobutane has, as isomers, a meso form and a dl form that is an optical isomer.

The dl form that is an optical isomer has a melting point (mp) of not higher than 0° C. (boiling point (bp): about 213° C.), and the dl form is a liquid at room temperature. In contrast with it, the meso form has a melting point of about 73° C. (boiling point: about 213° C.), and the meso form is a white solid at room temperature.

By utilizing a difference in the characteristics between the dl form and the meso form, they can be separated to a certain extent.

In the present invention, the content of the dl form having a low melting point in 100% by mass of 1,2,3,4-tetrachlorobutane that is a starting raw material is controlled to usually not less than 40% by mass. By controlling the amount of the dl form as above, the content of the meso form inevitably becomes usually not more than 60% by mass. By the use of 1,2,3,4-tetrachlorobutane containing the dl form and the meso form in such amounts, the temperature for dissolving the 1,2,3,4-tetrachlorobutane into a reaction solvent and the reaction temperature can be set low. On that account, cleavage of C—C bonds due to heating and excess fluorination is hard to proceed, and the desired product can be obtained with a high selectivity.

<Solvent>

The solvent (reaction solvent) for use in the present invention is desirably a compound which is hard to react with fluorine gas and can be maintained in a liquid state under the reaction conditions. Examples of such compounds include chlorocarbons and chlorofluorocarbons.

These solvents may be used singly or in combination thereof. Examples of the chlorocarbons employable as the reaction solvents in the present invention include tetrachloromethane and hexachloroethane. Examples of the chlorofluorocarbons employable as the reaction solvents in the present invention include trichlorotrifluoroethane and tetrachlorodifluoroethane.

The compounds wherein all of hydrogen atoms bonded to carbon atoms are substituted with halogen atoms such as chlorine atom and fluorine atom as described above are hard to cause substitution reaction even if they come into contact with fluorine gas, and 1,2,3,4-tetrachlorohexafluorobutane that is a desired product in the production process of the present invention can be efficiently produced. The 1,2,3,4-tetrachlorohexafluorobutane itself produced by the production process of the present invention may be used as a solvent, because it satisfies the aforesaid requirements of being hard to react with fluorine gas and capable of being maintained in a liquid state under the reaction conditions.

In such a reaction solvent as above for use in the production process of the present invention, hydrogen fluoride is preferably contained. When hydrogen fluoride is contained in the reaction solvent, 1,2,3,4-tetrachlorohexafluorobutane can be produced from the 1,2,3,4-tetrachlorobutane in a high yield with a high selectivity.

In the case where hydrogen fluoride is contained in the reaction solvent in the present invention, the amount of the hydrogen fluoride contained in the reaction solvent is usually not less than 5% by mass based on 100% by mass of the reaction solvent. In the present invention, the amount of the hydrogen fluoride in the reaction solvent is preferably in the range of 5 to 50% by mass. If the amount of the hydrogen fluoride is less than 5% by mass, the reaction rate of the fluorination reaction sometimes becomes slow. If the amount of the hydrogen fluoride is more than 50% by mass, the reaction readily proceeds and the amount of the low-boiling component tends to increase because of cleavage of C—C bonds and the like.

In the present invention, fluorination of 1,2,3,4-tetrachlorobutane is carried out using such a solvent as above, and therefore, even if a catalyst is not used, 1,2,3,4-tetrachlorohexafluorobutane can be produced in a satisfactory yield. By virtue of nonuse of the catalyst, an operation for separating the catalyst after completion of the production reaction can be omitted. These effects are markedly exerted especially when a solvent containing hydrogen fluoride is used as a reaction solvent.

<Feed of Fluorine Gas>

In the present invention, when fluorine gas is fed to 1,2,3,4-tetrachlorobutane using plural reactors in the presence of a solvent and in the absence of a catalyst to allow the 1,2,3,4-tetrachlorobutane and the fluorine gas to react with each other, a part or all of unreacted fluorine gas discharged from one reactor is introduced into a reactor different from said one reactor, whereby 1,2,3,4-tetrachlorohexafluorobutane is produced.

Although the constitution and the arrangement of the reactors to carry out such reaction are not specifically restricted, it is preferable in the present invention that the aforesaid plural reactors are arranged in series, the reactors are filled with the solvent and 1,2,3,4-tetrachlorobutane, the fluorine gas is fed to allow the 1,2,3,4-tetrachlorobutane and the fluorine gas to react with each other, and a part or all of unreacted fluorine gas discharged from a reactor on the upstream side is introduced into a reactor on the downstream side. By passing the fluorine gas in this manner, expensive fluorine gas can be used unwastefully and efficiently.

In order to use expensive fluorine gas efficiently, it is generally desirable to complete fluorination reaction of 1,2,3,4-tetrachlorobutane, but for the completion, it is necessary to introduce a large amount of fluorine gas into the reactor. As the reaction approaches completion, the probability of reaction of the introduced fluorine gas is lowered. Further, in order to maintain the pressure in the reactor in a defined range, it is necessary to discharge the gas having been introduced, and as a result, unreacted fluorine gas is frequently discharged wastefully. Since the fluorine gas is expensive, such a waste is very disadvantageous industrially.

The present inventors have now found that such a waste can be avoided by the following methods.

(1) A method comprising bringing 1,2,3,4-tetrachlorobutane and fluorine gas into contact with each other using plural reactors and introducing a part or all of unreacted fluorine gas discharged from one reactor into a reactor different from said one reactor.

(2) A method comprising bringing 1,2,3,4-tetrachlorobutane and fluorine gas into contact with each other in plural reactors arranged in series and introducing a part or all of unreacted fluorine gas discharged from a reactor on the upstream side into a reactor on the downstream side.

The method (2) is particularly preferable.

As the reactor, a pressure-resistant container in which a heating/cooling device, a stirring device, a gas blowing line having an inlet for introducing a gas into a liquid phase, and a gas discharge line for discharging a gas such as fluorine gas from a gas phase are arranged, for example, an autoclave can be used.

In the reaction in the production process of the present invention, fluorine gas having high corrosive properties is introduced into the reactor, and besides, hydrogen fluoride having high corrosive properties may be contained in the reaction solvent. Therefore, the parts brought into contact with a reaction solution, such as a reactor, a stirring device and a gas blowing line are formed from a material having resistance to corrosion by fluorine, hydrogen fluoride or the like. Examples of the materials having such corrosion resistance include Inconel (registered trademark), Hasteroy (registered trademark), e.g., particularly Hasteroy HC, SUS, and Teflon (registered trademark) lining of these materials. However, nickel that is sometimes included in the corrosion-resistant materials becomes a fluoride occasionally, and this fluoride accelerates substitution reaction between Cl and F. Therefore, it is preferable to use, as the corrosion-resistant material, a material having a low content of nickel.

In the present invention, the number of the plural reactors arranged in series is not specifically restricted, but if two reactors are arranged in series, expensive fluorine gas can be used unwastefully and efficiently in many cases. However, in the case where fluorine in the fluorine gas is not used up sufficiently even in the reactor on the downstream side, it is preferable that a part or all of unreacted fluorine gas discharged from the reactor on the downstream side is introduced into the reactor on the upstream side, or the number of reactors is changed to three or more and a part or all of unreacted fluorine gas is introduced into a reactor on further downstream side.

An embodiment for carrying out the present invention is described below in detail with reference to an example wherein two reactors are arranged in series. In the following description, of the two reactors, a reactor on the upstream side is referred to as a "first reactor", and a reactor on the downstream side is referred to as a "second reactor".

Two reactors are arranged in series, then 1,2,3,4-tetrachlorobutane that is a starting raw material is introduced into these reactors, and into the reactors, such a solvent (reaction solvent) as above is further introduced. In this case, the 1,2,3,4-tetrachlorobutane is introduced in such a way that the concentration of the 1,2,3,4-tetrachlorobutane which is a starting raw material and is present in the reactors is usually 10 to 50% by mass.

By dissolving such an amount of the 1,2,3,4-tetrachlorobutane in the reaction solvent and carrying out fluorination reaction, the following three advantages are obtained.

(1) The reaction efficiency is good.

(2) Even in the case where the content of the meso form in the 1,2,3,4-tetrachlorobutane is relatively high, it is unnecessary to carry out heating for dissolving the meso form, or even if heating is carried out, the heating temperature can be lowered.

(3) Cleavage of C—C bonds of the 1,2,3,4-tetrachlorobutane, etc. are hard to occur.

After the 1,2,3,4-tetrachlorobutane and the reaction solvent are introduced into the reactors, air in the reactors is preferably replaced with an inert gas such as nitrogen gas, helium gas, neon gas or argon gas, in order to suppress formation of oxygen-containing impurities.

After the 1,2,3,4-tetrachlorobutane that is a starting raw material is dissolved in the solvent containing hydrogen fluoride as described above, or after air in the reactors is replaced with an inert gas subsequently to the dissolving operation, fluorine gas is introduced into the first reactor through a gas blowing line having an inlet in the liquid phase to fluorinate the 1,2,3,4-tetrachlorobutane. A part or all of unreacted fluorine gas after the reaction in the first reactor is introduced into a gas blowing line having an inlet in the liquid phase of the second reactor through a gas discharging line provided in the gas phase. It is also possible that fluorine gas is freshly introduced into the second reactor in addition to the unreacted fluorine gas after the reaction in the first reactor.

The fluorine gas introduced into the first reactor through the gas blowing line of the first reactor may be simple fluorine gas, but in usual, a dilute mixed gas obtained by diluting fluorine gas with the aforesaid inert gas is introduced. When the dilute mixed gas is used, the concentration of the fluorine gas in the dilute mixed gas is usually not less than 30% by volume, and it is preferable to use a dilute mixed gas having fluorine gas concentration of 40 to 70% by volume.

That is to say, if a dilute mixed gas having the concentration of the fluorine gas of less than 30% by volume is used, the reaction rate is slow, resulting in an industrial disadvantage in some cases. If a dilute mixed gas having a fluorine concentration of more than 70% by volume is used, the reaction control is difficult, and cleavage of C—C bonds is liable to occur, and besides, side reactions such as excess fluorination reaction tend to easily proceed.

Accordingly, in order to industrially prepare 1,2,3,4-tetrachlorohexafluorobutane in a higher yield with a higher selectivity, it is preferable to set the concentration of the fluorine gas in the dilute mixed gas in the range of 30 to 70% by volume. The dilute mixed gas is preferably introduced into the liquid phase through the gas blowing line.

The feed rate of the dilute mixed gas introduced into the first reactor depends upon the concentration of the fluorine gas, and when the concentration of the fluorine gas is, for example, 40 to 50% by volume, the dilute mixed gas is fed at such a rate that the quantity of the gas fed per minute is 1/30 to 1/2, preferably 1/15 to 1/4, of the volume of the first reactor.

The fluorine gas, the concentration of which has been set in the range of 30 to 70% by volume and which has been introduced into the liquid phase of the first reactor as above, is consumed in the fluorination reaction with the 1,2,3,4-tetrachlorobutane. And a part or all of the discharged gas from the gas phase portion of the first reactor after the reaction is introduced into the second reactor. The discharged gas contains fluorine gas which has not undergone reaction in the first reactor, and this is consumed in the second reactor. From the gas discharging line installed in the gas phase portion of the second reactor, a diluent gas is mainly discharged. The reason is that almost all of the fluorine gas has been consumed in the second reactor. The concentration of the fluorine gas contained in the discharged gas from the second reactor is preferably not more than 10% by volume, more preferably not more than 2% by volume.

By using the first reactor and the second reactor arranged in series in the above manner, expensive fluorine gas can be efficiently used without loss. That is to say, the purpose of the second reactor is that the fluorine gas lost from the first reactor is recovered and effectively used.

The discharged gas containing fluorine gas, which has been discharged from the first reactor as above, is introduced as it is into the liquid phase portion of the second reactor and used for fluorination reaction of the 1,2,3,4-tetrachlorobutane in the second reactor. As described above, if the concentration of the fluorine gas is less than 30% by volume, the reaction rate is sometimes slow, and therefore, it is also possible that fluorine gas is freshly added and allowed to undergo reaction according to circumstances.

The volume of the second reactor is preferably not more than the volume of the first reactor, and more preferably not more than 2/3 of the volume of the first reactor. In order to increase absorption efficiency of the fluorine gas, the reaction container preferably has a structure that is long and thin in the vertical direction.

The present invention is a process in which when fluorine gas is fed to 1,2,3,4-tetrachlorobutane using plural reactors in the presence of a solvent and in the absence of a catalyst to allow the 1,2,3,4-tetrachlorobutane and the fluorine gas to react with each other, a part or all of unreacted fluorine gas discharged from one reactor is introduced into a reactor different from said one reactor, whereby 1,2,3,4-tetrachlorohexafluorobutane is produced. It is preferable that the above-mentioned plural reactors are arranged in series and a part or all of unreacted fluorine gas discharged from a reactor on the upstream side is introduced into a reactor on the downstream-side, whereby expensive fluorine gas can be used efficiently. That is to say, the present invention is an economical process for producing 1,2,3,4-tetrachlorohexafluorobutane in which expensive fluorine gas is effectively utilized.

The reaction temperature of the fluorination reaction is set in the range of usually −20 to 70° C., preferably 0 to 50° C. By setting the reaction temperature as above, cleavage of C—C bonds of the 1,2,3,4-tetrachlorobutane, excess fluorination, etc. are hard to occur.

In such a temperature range as above, the reaction pressure of the fluorination reaction is set in the range of 0.1 to 2.0 MPa.

[Process for Purifying 1,2,3,4-tetrachlorohexafluorobutane]

By performing the reaction as above, the 1,2,3,4-tetrachlorobutane is fluorinated, and at least a part of it becomes 1,2,3,4-tetrachlorohexafluorobutane. As most of this 1,2,3,4-tetrachlorohexafluorobutane is present in a dissolved state in the reaction solvent, in the reaction solution after the above reaction, the reaction solvent, hydrogen fluoride, 1,2,3,4-tetrachlorobutane that is a raw material, 1,2,3,4-tetrachlorohexafluorobutane produced by the reaction, and besides, side reaction products, etc. are contained.

Since the desired product of the production process of the present invention is 1,2,3,4-tetrachlorohexafluorobutane, it is necessary to separate 1,2,3,4-tetrachlorohexafluorobutane that is the desired product from the reaction solution obtained as above.

For separation and purification of the 1,2,3,4-tetrachlorohexafluorobutane, a purification process by distillation using a distillation column is advantageous. In the process for purifying 1,2,3,4-tetrachlorohexafluorobutane of the present invention, purification of 1,2,3,4-tetrachlorohexafluorobutane by distillation is carried out using preferably two or more distillation columns. In this case, the number of theoretical plates in at least one of the distillation columns needs to be usually 15 or more, more preferably 25 or more. If the number of theoretical plates is less than 15, separation of impurities, particularly tetrachloropentafluorobutane ($C_4HCl_4F_5$) and the like, is insufficient. When the number of theoretical plates is 15 or more, 1,2,3,4-tetrachlorohexafluorobutane that is a desired product can be sufficiently separated from the tetrachloropentafluorobutane, and 25 or more theoretical plates are preferable because separation performance is further improved.

The process for separation and purification is, for example, a process comprising introducing the reaction solution containing 1,2,3,4-tetrachlorohexafluorobutane into the first distillation column using a liquid transport pump or the like to separate the reaction solution into a low-boiling substance and a high-boiling substance (liquid containing the solvent having been used for the reaction and liquid containing 1,2,3,4-tetrachlorohexafluorobutane). The 1,2,3,4-tetrachlorohexafluorobutane that is a desired product may be obtained as a low-boiling substance from the column top of the first distillation column, but in usual, it is obtained as a high-boiling substance from the column bottom of the first distillation column. And if necessary, it may be obtained from the column top of the second distillation column by introducing it into the second distillation column. Moreover, it is also possible to carry out purification by performing the same operation using the third and the fourth distillation columns, when needed.

The 1,2,3,4-tetrachlorohexafluorobutane thus obtained is sometimes contaminated with hydrogen fluoride, a slight amount of fluorine gas, etc., and therefore, this 1,2,3,4-tetrachlorohexafluorobutane is brought into contact with an alkaline substance and/or water to remove hydrogen fluoride, etc. This step may be carried out prior to introduction into the first distillation column according to circumstances, or it may be carried out between the first distillation column and the second distillation column according to circumstances.

Examples of the alkaline substances for use in the present invention include alkali metal compounds such as sodium hydroxide, potassium hydroxide and lithium hydroxide, and alkaline earth metal compounds such as calcium hydroxide. These alkaline substances are usually used after they are dissolved or dispersed in water.

By bringing such an alkaline substance into contact with the 1,2,3,4-tetrachlorohexafluorobutane, acid components such as hydrogen fluoride and fluorine gas form salts to move into the aqueous phase. As water is hardly dissolved in the 1,2,3,4-tetrachlorohexafluorobutane, (solubility<300 wt ppm), two-layer separation is possible.

Further, as a slight amount of water is contained in the 1,2,3,4-tetrachlorohexafluorobutane having been brought into contact with water as above, it is preferable to bring the 1,2,3,4-tetrachlorohexafluorobutane into contact with a porous purifying agent to remove water contained therein.

Examples of the porous purifying agents used herein include a carbonaceous solid material, alumina and zeolite. In the present invention, molecular sieves 3A, 4A, 5A and the like are particularly preferably used. The temperature in the contact step with such porous purifying agents is preferably in the range of 0 to 60° C.

The 1,2,3,4-tetrachlorohexafluorobutane thus purified has a purity of usually not less than 98% by mass, preferably not less than 99% by mass.

The yield of the 1,2,3,4-tetrachlorohexafluorobutane based on the starting raw material is usually not less than 70% by mol, and 1,2,3,4-tetrachlorohexafluorobutane having a high purity can be obtained very efficiently.

On the other hand, a low-boiling substance (liquid containing a solvent having been used for the reaction) which has been separated from the 1,2,3,4-tetrachlorohexafluorobutane by the distillation column as described above can be used as a reaction solvent for the fluorination of 1,2,3,4-tetrachlorobutane, and can be recycled by returning it to the reactor for carrying out the fluorination reaction. When at least apart of the reaction solvent is recycled, the low-boiling substance may be purified, if necessary, prior to recycling.

The reaction solvent is not fluorinated by such fluorination reaction as above, that is, it does not consume fluorine. Hence, recycling of at least a part of the reaction solvent is industrially advantageous.

EXAMPLES

The production process and the purification process for 1,2,3,4-tetrachlorohexafluorobutane of the present invention are further described with reference to the following examples, but it should be construed that the present invention is in no way limited to those examples.

Example of Raw Material

Chlorination reaction of 1,3-butadiene produced industrially was carried out to mainly produce 3,4-dichlorobutene-1 and 1,4-dichlorobutene-2. Isomerization reaction of 1,4-dichlorobutene-2 was carried out produce 3,4-dichlorobutene-1, and by-product was separated by distillation to obtain 3,4-dichlorobutene-1. The 3,4-dichlorobutene-1 was analyzed by gas chromatography, and as a result, the purity thereof was 99.3% by mol. This 3,4-dichlorobutene-1 was chlorinated with chlorine gas in the absence of a solvent, and the resulting mixture was separated and purified by distillation to obtain 1,2,3,4-tetrachlorobutane. The 1,2,3,4-tetrachlorobutane was analyzed by gas chromatography, and as a result, the purity thereof was 99.1% by mol, and the ratio of dl form/meso form was about 49/51.

Example 1

As the first reactor, a SUS304 reactor (Teflon (trade mark) lining) having an internal volume of 1000 ml was used. Into this reactor, a solution obtained by dissolving 20 g of hydrogen fluoride in 380 g of tetrachloromethane as a solvent and 100 g of 1,2,3,4-tetrachlorobutane obtained in the above "Example of raw material" were charged, and nitrogen gas was introduced at a pressure of 1.0 MPa to carry out leakage test. Then, the nitrogen gas was purged, and the temperature was maintained at 35° C. while stirring.

Thereafter, an outlet gas line (discharging line) provided in the gas phase portion of the first reactor was connected to an inlet of the second reactor. As the second reactor, a SUS304 reactor (Teflon (trade mark) lining) having an internal volume of 1000 ml was used. Into this reactor, a solution obtained by dissolving 20 g of hydrogen fluoride in 380 g of tetrachloromethane as a solvent and 100 g of 1,2,3,4-tetrachlorobutane obtained in the above "Example of raw material" were charged, and nitrogen gas was introduced at a pressure of 1.0 MPa to carry out leakage test. Then, the nitrogen gas was purged, and the temperature was maintained at 30° C. while stirring.

Thereafter, while maintaining the temperature of the first reactor at 35° C. and stirring, fluorine gas of 50% by volume obtained by dilution with nitrogen gas was continuously fed to the liquid phase portion at a pressure of 0.2 MPa and a feed rate of 100 ml/min through a gas introducing pipe installed in the reactor to initiate the reaction. After about 5 hours from the initiation of the reaction, the fluorine gas concentration in the outlet (gas discharging line) gas of the first reactor was 5% by volume (the remainder was mainly nitrogen gas).

The outlet (gas discharging line) gas of the first reactor was continuously introduced into the liquid phase portion of the second reactor. While maintaining the reaction temperature in the second reactor at 30° C. and stirring, the gas introduced from the outlet of the first reactor was allowed to undergo reaction. As a result, in the outlet (gas discharging line) gas of the second reactor, fluorine gas was not detected at all.

After the lapse of about 21 hours from the initiation of the reaction, the fluorine gas concentration in the outlet (gas discharging line) gas of the first reactor was 30% by volume (the remainder was mainly nitrogen gas). On the other hand, the outlet gas of the second reactor was analyzed, and as a result, fluorine gas was not detected at all in the outlet gas of the second reactor.

At this point of time (21 hours after the initiation of the reaction), feed of a feed gas (fluorine gas of 50% by volume) was temporarily stopped, and analysis of the product in the first reactor was carried out. As a result, the yield of produced 1,2,3,4-tetrachlorohexafluorobutane which was a desired product (number of moles of 1,2,3,4-tetrachlorohexafluorobutane/number of moles of fed 1,2,3,4-tetrachlorobutane, the same shall apply hereinafter) was 74% by mol. At this point of time, the fluorine gas utilization of the first reactor and the second reactor was about 100%.

Thereafter, the feed gas (fluorine gas of 50% by volume) was fed in the same manner as above to initiate the reaction again. After about 32 hours from the initiation of the reaction, the fluorine gas concentration in the outlet gas of the first reactor was about 50% by volume, and the reaction in the first reactor was completed. At this point of time, the fluorine gas concentration in the outlet gas of the second reactor was not more than 0.1% by volume. At this point of time, feed of the feed gas (fluorine gas of 50% by volume) was stopped, and analysis of the product in the first reactor was carried out. As a result, the yield of 1,2,3,4-tetrachlorohexafluorobutane which was a desired product was 78% by mol.

As is clear from the results, by the use of two reactors, expensive fluorine gas can be efficiently used without loss, and 1,2,3,4-tetrachlorohexafluorobutane which is a desired product can be obtained in a high yield.

Example 2

A solution containing crude 1,2,3,4-tetrachlorohexafluorobutane obtained by repeating reaction under the conditions of [Example 1] was charged into a distillation column (number of theoretical plates: 15) and distilled. The resulting high-boiling substance was brought into contact with a potassium hydroxide aqueous solution and subjected to dehydration treatment at 18° C. using zeolite (molecular sieves 4A). The high-boiling substance having been subjected to the above treatment was charged into a distillation column (number of theoretical plates: 25) and subjected to separation and purification to obtain 1,2,3,4-tetrachlorohexafluorobutane which was a desired product and mainly tetrachloromethane. As a result of analysis by gas chromatography, the purity of the 1,2,3,4-tetrachlorohexafluorobutane was about 99.8% by mass.

Example 3

As the first reactor, a SUS reactor having an internal volume of 1000 ml was used. Into this reactor, a solution (as a solvent) obtained by dissolving 20 g of hydrogen fluoride in 380 g of 1,2,3,4-tetrachlorohexafluorobutane obtained in [Example 2] and 100 g of 1,2,3,4-tetrachlorobutane obtained in the above "Example of raw material" were charged, and nitrogen gas was introduced at a pressure of 1.0 MPa to carry out leakage test. Then, the nitrogen gas was purged, and the temperature was maintained at 40° C. while stirring.

Thereafter, an outlet gas line (discharging line) provided in the gas phase portion of the first reactor was connected to an inlet of the second reactor. As the second reactor, a SUS304 reactor having an internal volume of 1000 ml was used. Into this reactor, a solution (as a solvent) obtained by dissolving 20 g of hydrogen fluoride in 300 g of 1,2,3,4-tetrachlorohexafluorobutane obtained in Example 2 and 80 g of 1,2,3,4-tetrachlorobutane obtained in the above "Example of raw material" were charged, and leakage test was carried out in the same manner as in the first reactor. Then, the temperature was maintained at 35° C. while stirring.

Thereafter, while maintaining the temperature of the first reactor at 40° C. and stirring, fluorine gas of 40% by volume obtained by dilution with nitrogen gas was continuously fed to the liquid phase portion at a pressure of 0.2 MPa and a feed rate of 100 ml/min through a gas introducing pipe installed in the reactor to initiate the reaction.

After about 5 hours from the initiation of the reaction, the fluorine gas concentration in the outlet (gas discharging line) gas of the first reactor was 3% by volume (the remainder was mainly nitrogen gas). The discharged gas from the outlet (gas discharging line) of the first reactor was continuously introduced into the liquid phase portion of the second reactor to subject the gas to reaction at a reaction temperature of 35° C. while stirring. In this case, fluorine gas was not detected at all in the outlet (gas discharging line) gas of the second reactor.

After the lapse of about 26 hours from the initiation of the reaction, the fluorine gas concentration in the outlet (gas discharging line) gas of the first reactor was about 22% by volume (the remainder was mainly nitrogen gas). On the other hand, the outlet gas of the second reactor was analyzed, and as a result, fluorine gas was not detected at all in the outlet gas of the second reactor.

At this point of time (about 26 hours after the initiation of the reaction), feed of a feed gas (fluorine gas of 40% by volume) was temporarily stopped, and analysis of the product in the first reactor was carried out. As a result, the yield of 1,2,3,4-tetrachlorohexafluorobutane which was a desired product was 76% by mol. At this point of time, the fluorine gas utilization rates of the first reactor and the second reactor were about 100%.

Thereafter, the feed gas (fluorine gas of 40% by volume) was fed in the same manner as above to initiate the reaction again. After about 45 hours from the initiation of the reaction, the fluorine gas concentration in the outlet gas of the first reactor was about 40% by volume, and the reaction in the first reactor was completed. At this point of time, the fluorine gas concentration in the outlet gas of the second reactor was not more than 0.1% by volume.

At this point of time, feed of the feed gas (fluorine gas of 40% by volume) was stopped, and analysis of the product in the first reactor was carried out. As a result, the yield of 1,2,3,4-tetrachlorohexafluorobutane which was a desired product was 80% by mol.

The invention claimed is:

1. A process for producing 1,2,3,4-tetrachlorohexafluorobutane, comprising feeding fluorine gas to 1,2,3,4-tetrachlorobutane using plural reactors in the presence of a solvent containing hydrogen fluoride and in the absence of a catalyst to allow the 1,2,3,4-tetrachlorobutane and the fluorine gas to react with each other, wherein
the plural reactors are comprised of a first reactor on an upstream side and a second reactor on a downstream side and are arranged in series, and a part or all of unreacted fluorine discharged from the first reactor is introduced into the second reactor,
the concentration of fluorine gas in a dilute mixed gas introduced into the first reactor is not less than 30% by volume, and
the concentration of fluorine gas contained in discharged gas from the second reactor is not more than 10% by volume.

2. The process for producing 1,2,3,4-tetrachlorohexafluorobutane as claimed in claim 1, wherein a part or all of unreacted fluorine gas discharged from a reactor on the downstream side is further introduced into a reactor on the upstream side.

3. The process for producing 1,2,3,4-tetrachlorohexafluorobutane as claimed in claim 1, wherein in 100% by mass of the 1,2,3,4-tetrachlorobutane, a dl form that is an optical isomer thereof is contained in an amount of not less than 40% by mass.

4. The process for producing 1,2,3,4-tetrachlorohexafluorobutane as claimed in claim 1, wherein the reaction solution containing 1,2,3,4-tetrachlorohexafluorobutane obtained by the reaction of the 1,2,3,4-tetrachlorobutane with the fluorine gas is introduced into a distillation column,
the reaction solution is separated into a liquid containing 1,2,3,4-tetrachlorohexafluorobutane and a liquid containing the solvent, and
the separated liquid containing the solvent is returned to a reactor for carrying out reaction of 1,2,3,4-tetrachlorobutane with fluorine gas and recycled.

5. A process for purifying 1,2,3,4-tetrachlorohexafluorobutane, comprising:
introducing a reaction solution containing 1,2,3,4-tetrachlorohexafluorobutane obtained in the process as claimed in claim 1 into a distillation column,
separating the reaction solution into a liquid containing 1,2,3,4-tetrachlorohexafluorobutane and a liquid containing the solvent, and
bringing at least a part of the separated liquid containing 1,2,3,4-tetrachlorohexafluorobutane into contact with an alkaline substance and/or water.

6. The process for purifying 1,2,3,4-tetrachlorohexafluorobutane as claimed in claim 5, wherein the liquid containing 1,2,3,4-tetrachlorohexafluorobutane which has been brought into contact with an alkaline substance and/or water is further brought into contact with a porous purifying agent.

7. The process for purifying 1,2,3,4-tetrachlorohexafluorobutane as claimed in claim 6, wherein the porous purifying agent is zeolite.

8. The process for producing 1,2,3,4-tetrachlorohexafluorobutane as claimed in claim 2, wherein the plural reactors are two reactors arranged in series.

* * * * *